(12) United States Patent
Eagen et al.

(10) Patent No.: US 6,484,580 B2
(45) Date of Patent: Nov. 26, 2002

(54) IN SITU TESTING OF A SATELLITE OR OTHER OBJECT PRIOR TO DEVELOPMENT

(75) Inventors: James H. Eagen, Purcellville, VA (US); Michael Vujcich, Superior, CO (US); Terry D. Scharton, Santa Monica, CA (US)

(73) Assignee: Ball Aerospace & Technologies Corp., Boulder, CO (US)

( * ) Notice: Subject to any disclaimer, the term of this patent is extended or adjusted under 35 U.S.C. 154(b) by 38 days.

(21) Appl. No.: 09/809,683

(22) Filed: Mar. 14, 2001

(65) Prior Publication Data

US 2001/0032510 A1 Oct. 25, 2001

Related U.S. Application Data

(60) Provisional application No. 60/189,523, filed on Mar. 15, 2000.

(51) Int. Cl.[7] .................................. G01N 29/12; G01M 7/00
(52) U.S. Cl. ............................ 73/571; 73/579; 73/663; 73/432.1; 73/865.6
(58) Field of Search .................... 73/625, 626, 571, 73/579, 584, 583, 432.1, 586, 628, 663, 665, 865.6

(56) References Cited

U.S. PATENT DOCUMENTS

| 3,104,543 | A | * | 9/1963 | Kaminski ..................... 73/571 |
|---|---|---|---|---|
| 3,198,007 | A | | 8/1965 | Overton ......................... 73/69 |
| 3,827,288 | A | * | 8/1974 | Fletcher et al. ................ 181/5 |
| 4,397,187 | A | | 8/1983 | Stribling ...................... 73/589 |
| 4,574,632 | A | * | 3/1986 | Woolley et al. ......... 116/137 R |
| 4,644,794 | A | | 2/1987 | Vaicaitis ....................... 73/583 |
| 5,039,228 | A | * | 8/1991 | Chalmers .................... 374/141 |
| 5,138,884 | A | | 8/1992 | Bonavia ....................... 73/662 |
| 5,226,326 | A | | 7/1993 | Polen et al. .................. 73/571 |
| 5,251,497 | A | * | 10/1993 | Bressan ..................... 73/865.6 |
| 5,355,417 | A | | 10/1994 | Burdisso et al. .............. 351/71 |
| 5,601,083 | A | * | 2/1997 | Anderson ................... 600/443 |
| 6,031,486 | A | * | 2/2000 | Anderson et al. ........... 342/165 |

* cited by examiner

Primary Examiner—Daniel S. Larkin
Assistant Examiner—Rose M. Miller
(74) Attorney, Agent, or Firm—Sheridan Ross P.C.

(57) ABSTRACT

A method and system for testing a test object, such as a satellite, is disclosed. High energy acoustic testing is performed on the object by assembling an acoustical system about the test object rather than transporting the test object to a specially configured acoustic chamber. The acoustic system of the present invention preferably provides and directs acoustic energy directly to the surfaces of the test object rather than providing the test object in a high energy acoustic environment where a substantial amount of the acoustic energy is randomly directed within a chamber having the test object. Additionally, the present invention further provides for mechanical vibration tests concurrently or serially with acoustic testing, wherein the object is not required to be transported.

21 Claims, 8 Drawing Sheets

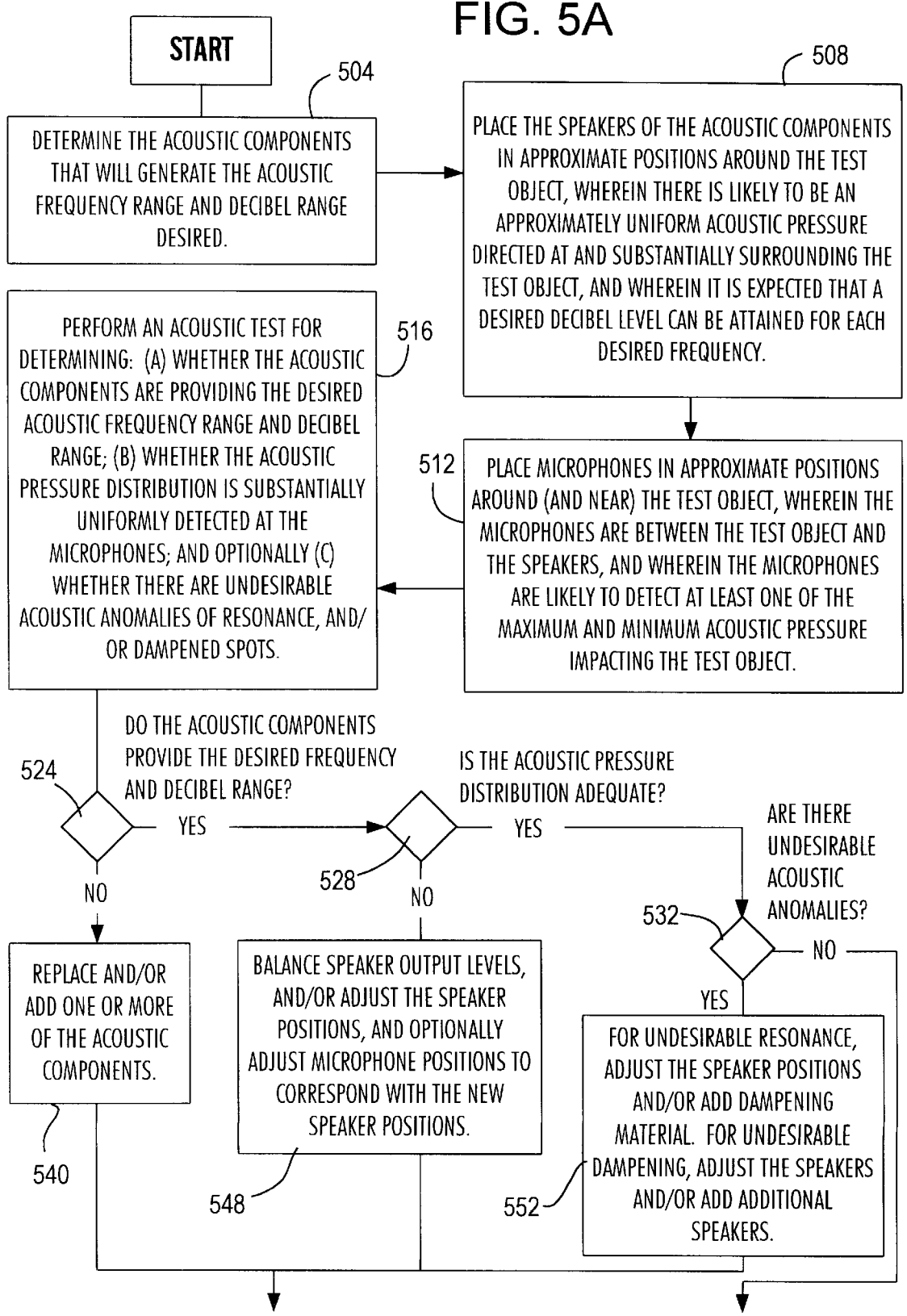

IN SITU TESTING OF A SATELLITE OR OTHER OBJECT PRIOR TO DEVELOPMENT

Figure 1:
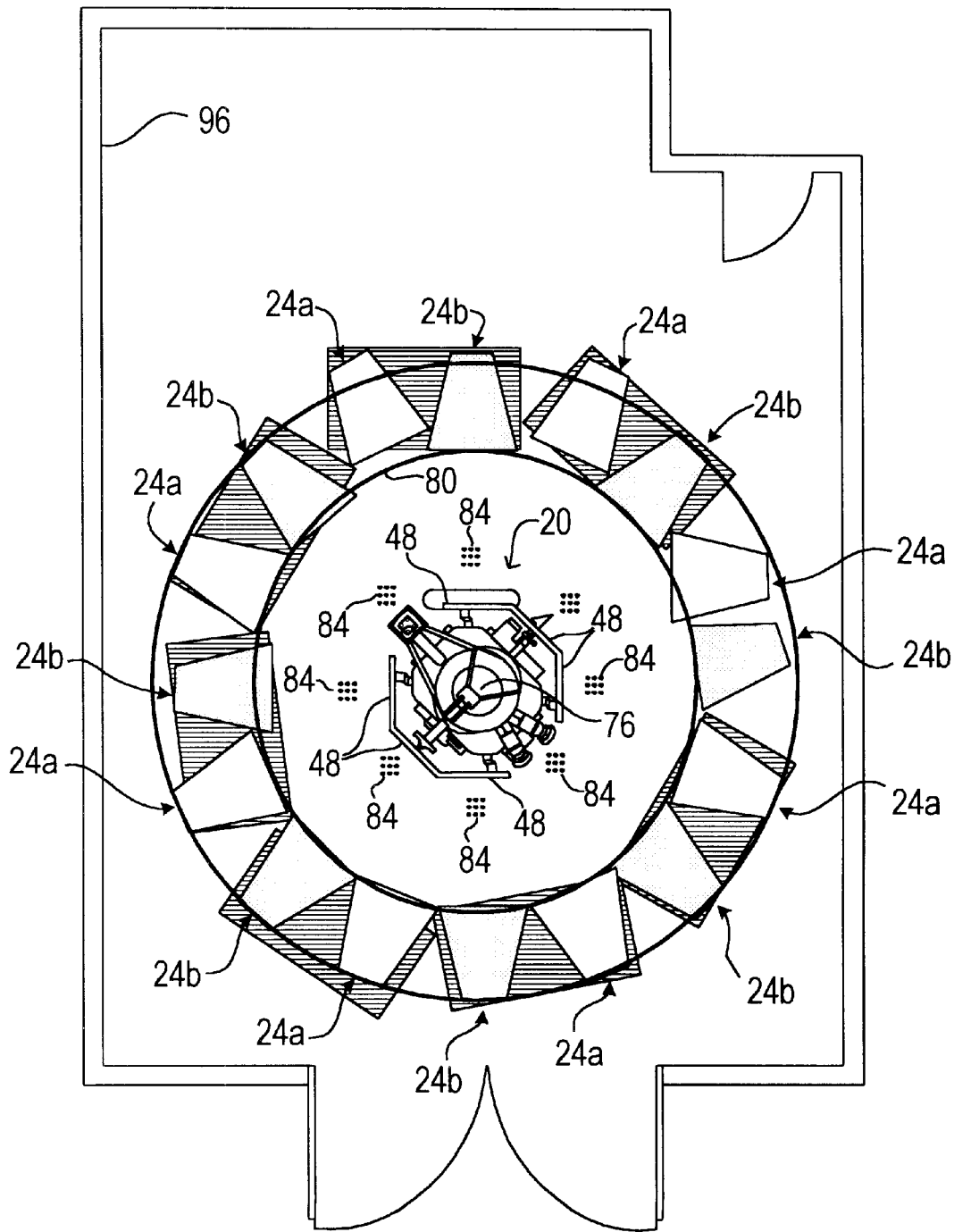

This application is related to and claims priority from Provisional Patent Application No. 60/189,523 filed Mar. 15, 2000.

The invention described herein was made in the performance of work under a NASA contract, and is subject to the provisions of Public Law 96–517 (35 U.S.C. 202) in which the Contractor has elected to retain title.

FIELD OF INVENTION

The present invention is a method and system for testing the reliability of an object such as a satellite prior to deployment, and more particularly provides a method and system for subjecting the object to high intensity acoustic energy by assembling an acoustic system about the object rather than transporting the object to location for performing such acoustic testing. Moreover, the present invention also provides for performing other types of tests without transporting the object. In particular, the present invention provides for performing mechanical vibration tests on the object in the same location as the acoustic testing of the object is performed.

BACKGROUND OF INVENTION

In the manufacturing assembly of objects, such as satellites, that are subject to extreme conditions during operation, various types of qualification or certification testing are typically performed on the object to determine whether the object can withstand the extreme conditions and still perform its intended functions. For example, it may be desirable to perform high energy acoustic tests of the object (e.g., a satellite) to determine whether various components of the object can withstand a high energy acoustic environment and still perform adequately. In particular, such acoustic testing is desirable for high surface area and low mass components such as solar panels. Moreover, it may also be desirable to perform other types of tests such as mechanical vibration tests on such objects.

Heretofore, to acoustically test an object such as a satellite prior to launch, the satellite would be transported to a specially configured reverberant acoustic chamber for subjecting the satellite to a uniform high energy acoustic environment. The transportation of the satellite is time consuming, expensive, and subjects the satellite to risks that are preferably avoided. Accordingly, it would be advantageous to perform high energy acoustic testing using a transportable acoustic system that can be assembled about the satellite without requiring the satellite to be moved. Moreover, it would be also be advantageous to provide a plurality of different types of qualification or certification tests to an object such as a satellite without moving the satellite between a plurality of testing stations. In particular, it would be advantageous to provide acoustic testing and mechanical vibration testing without the necessity of moving the satellite between various testing stations.

SUMMARY OF INVENTION

The present invention is a method and system for performing acoustic testing of a test object, such as a satellite, for thereby determining whether the test object is able to properly function when and/or after being subjected to high intensity acoustic energy. In particular, the present invention provides a method and system for at least partially surrounding the test object with high output acoustic speakers for directing acoustic energy directly at the test object for a specific desired range of test frequencies and corresponding decibel levels.

Prior to performing such an acoustic test, the present invention also provides a method for acoustically calibrating the speaker outputs so that the desired frequency range and corresponding decibels are achieved substantially uniformly about the test object. In particular, the speakers together with microphones for monitoring speaker acoustic output, are configured in initial positions around the test object. The speakers are expected to yield an approximately uniform acoustic distribution about the test object and the microphones are distributed around and substantially near the test object for measuring the acoustics impacting the test object. Accordingly, for each of a plurality of desired and/or predetermined acoustic frequencies and corresponding decibel levels, it is an aspect of the present invention to use the measurements obtained from the microphones to:

(a) determine whether the frequencies and corresponding decibel levels can be achieved by the speakers and related acoustical components (e.g., amplifiers) for electrically driving and controlling the acoustic output of the speakers;

(b) electronically and/or physically adjust the speaker outputs for obtaining a substantially uniform acoustic pressure about at least the portion of the test object identified as most vulnerable to a malfunction induced by the impact of high acoustic energy; and (c) further adjust the speaker outputs and/or provide additional modifications to the acoustical environment for alleviating or reducing localized acoustical anomalies such as resonance build-ups.

Thus, a result of the calibrating of the speaker outputs is that during actual testing of the test object, various speakers may be powered at different levels and, the speakers will be oriented so as to output a substantially uniform acoustic that varies substantially no more than, e.g., 6 dB about the test object.

Moreover, it is an aspect of the present invention to provide an acoustic environment altering material to the enclosure within which the acoustic calibration and testing is being performed so that an appropriate acoustic pressure level impacts the test object. In particular, it is an object of the present invention that a substantial amount of the acoustic energy output by the speakers directly impact the test object at a substantially normal angle to a surface of the test object. More particularly, when a satellite is the test object, it is an aspect of the present invention that such substantially normal acoustic impact be directed at high volume, low density portions of the satellite such as solar panels since these components are more likely to malfunction from high energy acoustics than other components. Accordingly, to reduce acoustic reflections and deflections, the acoustic altering material may be provided on the interior surface of the enclosure for dampening such reflected and/or deflected acoustic waves. Moreover, note that such dampening material may also reduce the intensity of localized relatively high energy acoustic build-ups in locations that might damage the test object as mentioned in (c) above.

Additionally, regarding (c) above, the present invention mitigates both high intensity and low intensity isolated acoustic anomalies substantially near the test object (wherein such anomalies might compromise what would otherwise be considered a substantially uniform acoustic test of the test object) by optionally providing partitions or other devices for directing or restricting a direction of the acoustic energy generated by the speakers.

Moreover, it is an aspect of the present invention that the speakers may be positioned at various distances and orientations from the test object. In particular, such speakers may be provided upon pedestals and/or at different heights relative to the test object. In particular, such speakers may be suspended as well as floor mounted for providing a plurality of acoustic sources that may generally hemispherically surround the test object.

It is also an aspect of the present invention that the test object may be acoustically tested without moving the test object from its area of manufacture since the acoustic generating portions of the present invention may be conveniently transported and positioned about the test object. Accordingly, the present invention may be used in place of transporting the test object to a specially engineered reverberant chamber for acoustically testing objects in a uniform acoustic environment having a very narrow acoustic variation between locations within the chamber.

Additionally, it is an aspect of the present invention that a plurality of different diagnostic or qualification tests can be performed without transporting the test object. In particular, mechanical vibration testing may be performed concurrently or serially with the acoustic testing of the present invention without transporting the test object.

Other features and benefits of the present invention will become evident from the accompanying drawings and the detailed description hereinbelow.

DETAILED DESCRIPTION

FIG. 1 shows a planar view of an embodiment of the present invention wherein the test object for acoustically being tested is a satellite 20. Accordingly, the satellite 20 is substantially surrounded by speaker assemblies 24a and 24b of the present invention for providing direct acoustic vibration to the satellite 20. In particular, the direct acoustic vibration (also known as acoustic pressure) is applied to the satellite 20 substantially simultaneously from all sides to thereby simulate at least the intensity of the acoustic pressure that is likely to be encountered by the satellite 20 during and/or after being launched into orbit. Thus, the acoustic test determines whether operable features of the satellite 20 remains operable during and/or after such testing.

Figure 2:
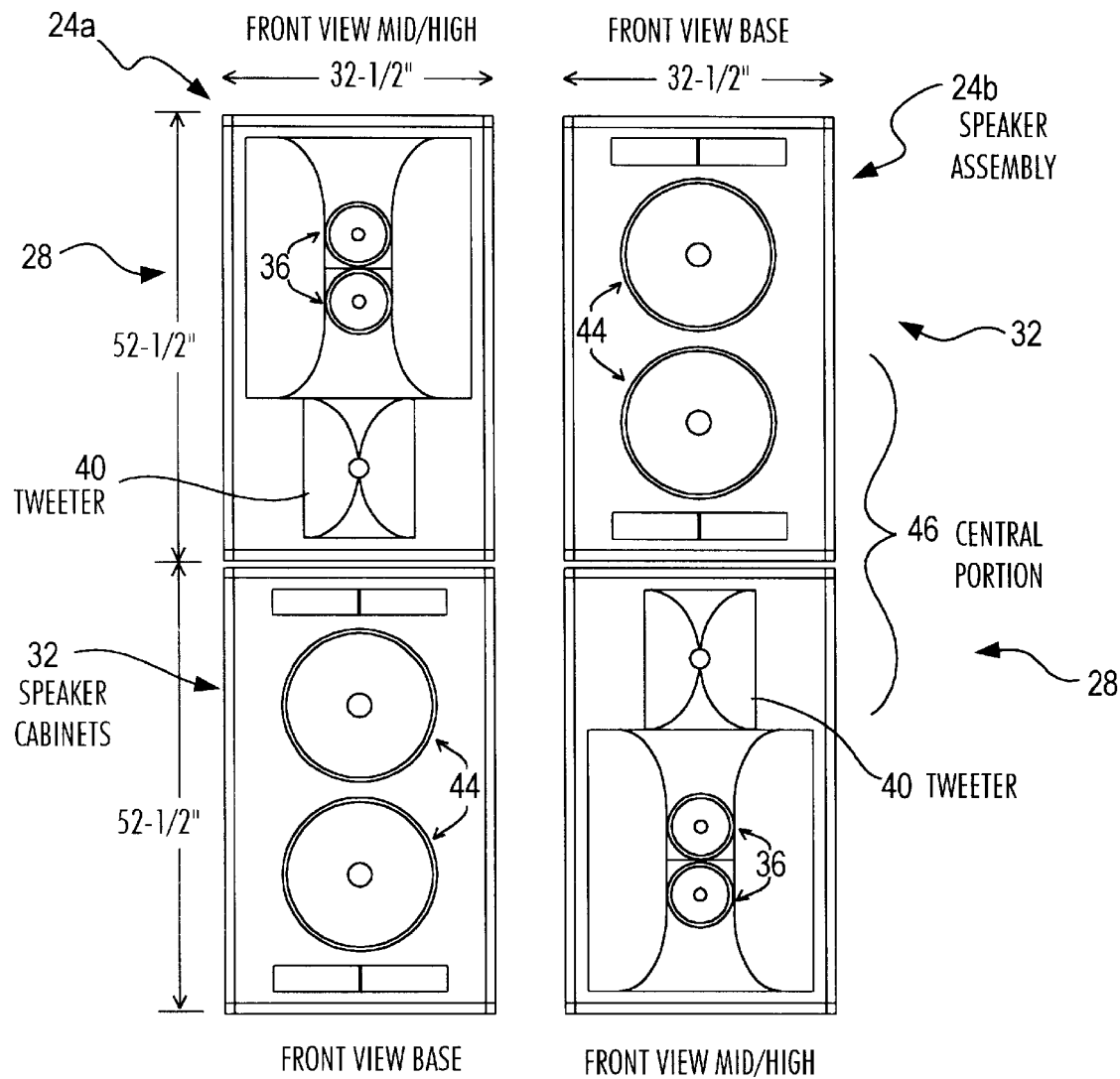

Two of the speaker assemblies 24a and 24b are shown in FIG. 2. Each speaker assembly 24a and 24b includes two speaker cabinets stacked one on top of the other, wherein one of the speakers is a mid/high range cabinet 28 and the other is a base speaker cabinet 32. In particular, the mid/high speaker cabinet 28 outputs acoustics in the range of 250 Hz to 1,200 Hz via midrange speakers and 1,200 Hz to 18,000 Hz via tweeters 40. Moreover, the base speakers 44 of the base speaker cabinet 32 outputs acoustics in the range of 37.5 Hz to 250 Hz via woofers 44. Further note that Table 1 hereinbelow provides specifications for each pair of stacked speaker cabinets 28 and 32.

TABLE 1

| | |
|---|---|
| Frequency Response: | 37.5 Hz to 18 kHz (±3 dB) |
| Enclosure tuning: | 37.5 Hz |
| Pressure Sensitivity: | 100 dB SPL 1 watt/1 meter - Low frequency |
| | 111 dB SPL 1 watt/1 meter - Mid frequency |
| | 116 dB SPL 1 watt/1 meter - High frequency |
| Power capacity: | 1600 watts continuous Pink noise LF |
| | 800 watts continuous Pink noise MF |
| | 100 watts continuous Pink noise HF |
| Crossover Frequency: | 250 Hz, 1200 Hz |

TABLE 1-continued

| | |
|---|---|
| Nominal Coverage Angles: | 30 degrees Horizontal |
| | 30 degrees Vertical |
| Nominal impedance: | 4 Ohms LF |
| | 8 Ohms MF |
| | 8 Ohms HF |

In the present embodiment, the speaker cabinets 28 and 32 were assembled by Audio Analysis Inc, Colorado Springs, Colo., and the speakers are powered by a combination of an amplifier rack, stereo graphic equalizer, and pink noise generator (all of which are not shown) as one skilled in the art will understand. Further, it should be noted that such speaker cabinets 28 and 32 are readily commercially available, and in particular, may be of the type used for large outdoor events.

The speaker assembly 24a is reversely stacked from that of the speaker assembly 24b such that their respective tweeters 40 remain in a central portion 46 along the vertical length of the speaker assemblies. This arrangement, together with the alternating of speaker assemblies 24a and 24b around the satellite 20 (FIG. 1) outputs desired acoustic wave signals to provide a substantially uniform direct acoustic pressure against one of: (a) at least the main portion of the satellite 20 that is most susceptible to acoustic pressure malfunction, e.g., at least the high surface area (or volume), low mass portions of the satellite 20 such as the solar panels 48, and (b) a majority of the surface area of the satellite. In particular, such direct acoustic energy output is applied to the solar panels 48 from substantially a normal direction to their photovoltaic surfaces since for high area-low mass satellite components such as the solar panels, acoustic energy from a substantially normal direction is most likely to induce the highest acoustic vibrational responses (e.g., the highest bending mode as one skilled in the art will understand). Note that this is also true for other high surface area (or volume) and low mass components, such as honey comb panels, antenna ground planes, thermal radiators, sheet metal panels and brackets, as one skilled in the art will understand.

Figure 3:
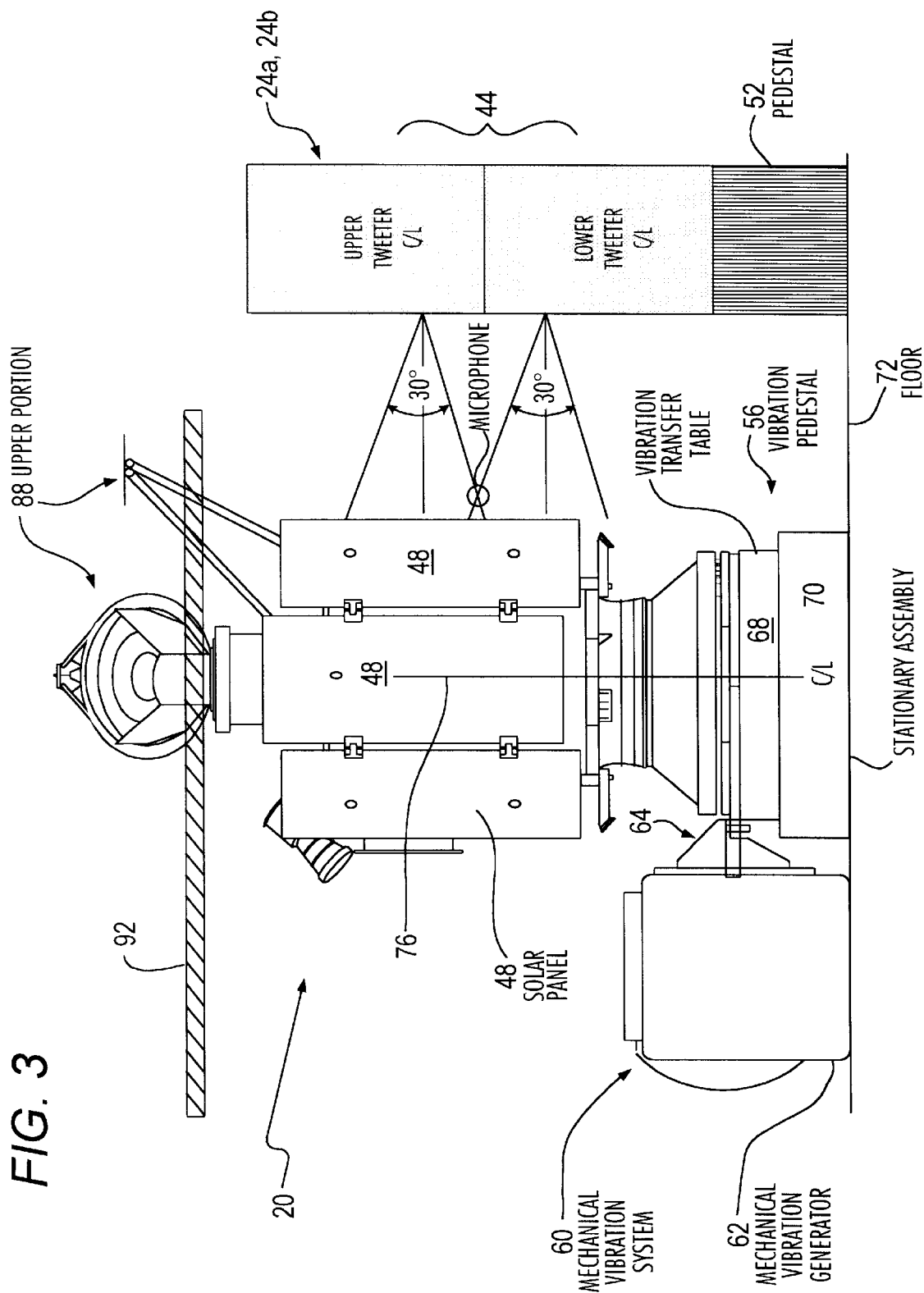

FIG. 3 shows the silhouette of a single pair of speaker assemblies 24a and 24b adjacent the satellite 20. As can be seen from this figure, the speaker assemblies 24a and 24b are elevated upon a pedestal 52. By elevating the speaker assemblies, their acoustic output aligns with the main body of the satellite 20 for substantially direct acoustic input thereto. Such pedestals 52 elevate each of the speaker assemblies 24a and 24b shown in FIG. 1. In particular, the pedestals 52 are desirable in the present embodiment due to the fact that the satellite 20 is provided upon a mechanical vibration pedestal 56 (FIG. 3), wherein mechanical vibration testing of the satellite 20 may also be performed either concurrently with or independently of the acoustic testing via the acoustic assemblies 24a and 24b. However, it is an important aspect of the present invention to have the ability to perform both acoustic and mechanical test without transporting the satellite 20 (or any other test object) from one testing area to another.

Accordingly, in addition to acoustic testing in the approximate range of 30 Hz to 10,000 Hz at decibels in the range of approximately 105 to 140 (relative to 20 microPascals), mechanical vibration testing may be performed that is of a substantially different character and uses substantially different testing techniques. For example, referring again to FIG. 3, there is a mechanical vibration system 60 having a mechanical vibration shaker 62 and also having therein the vibration pedestal 56 which is operatively linked by the linkage 64 to the vibration shaker 62. Moreover, the vibration pedestal 56 includes a vibration slip table 68 to which the linkage 64 is attached so that the vibration table is vibrationally movable upon a stationary assembly 70 (of the vibration pedestal 56). Thus, the stationary assembly 70 provides appropriate mechanical linkages (not shown) for allowing the vibration table 68 to transfer mechanical vibrations, received from the mechanical vibration generator 62, to the satellite 20 while the stationary assembly 70 remains fixedly attached to the floor 72.

Accordingly, the mechanical vibration system 60 vibrates test objects, such as the satellite 20, at lower frequencies and with, in general, substantially greater force than that provided by the acoustic testing procedures of the present invention. Moreover for test objects such as satellites or other spacecrafts, such mechanical vibration tests subject the test object to loads induced by the attachment of a base of the test object to a launch vehicle as opposed to the acoustic tests of the present invention for testing whether (certain components of) the test object can withstand the acoustic environment transmitted through the air during, e.g., launch and flight. In particular, the typical range of frequencies and amplitudes for vibrations of the mechanical vibration system 60 is 10 to 2,000 Hz of random vibration. Moreover, such mechanical vibrations vibrate substantially all components of the satellite 20 uniformly whereas the acoustic testing vibrates the external relatively low mass to surface area (or volume) components more than other satellite components.

Additionally, note that FIG. 3 also illustrates the advantage of orienting the speaker assemblies 24a and 24b as in FIG. 2, wherein the tweeters 40 are located in the central portion 46 of the vertical length of the speaker assemblies. In particular, the tweeters 40 of the speaker cabinets 28 have a relatively narrow acoustic transmission angular extent for transmitting high acoustic energy output in comparison to the other speakers 36 and 44. That is, the tweeters 40 have an approximately 30° transmission extent in comparison to the other speakers 36 and 44 which may have a transmission extent of 70° to 120°. Thus, in the present embodiment, the tweeters 40 create a limitation as to how close to the satellite 20 the speaker assemblies 24a and 24b may be positioned and still provide adequate acoustic pressure to a large portion of the satellite 20. However, the applicants of the present invention have discovered that adequate acoustic coverage at the desired frequencies and decibels may be obtained at a radial distance (from the central vertical axis 76) of approximately 1.3 meters beyond the outermost surfaces of the main portion of the satellite (e.g., the solar panels 48). Additionally, it is an aspect of the present invention that speaker assemblies having different acoustical characteristics from those illustrated in FIGS. 1–3 may be utilized in other embodiments of the present invention. Accordingly, the distances from the test object may vary depending on, e.g., the angular transmission extent of the speakers provided. Further note that acoustic coverage of a test object may be further enhanced by placing the speaker assemblies 24a and 24b (or alternative embodiments thereof) further away from the test object and by providing a spacer or additional speakers between the upper and lower stacked speaker cabinets 28 and 32. Thus, a test object that is taller than the satellite 20 may be substantially acoustically covered by the high frequency acoustic output of the 30° transmission extent of the tweeters 40 since: (a) there is a greater spacing between the tweeters, and (b) the tweeters are further away from a test object nearest surface to which the tweeters acoustic output is directed.

Returning to FIG. 1, note that the speaker assemblies 24a and 24b are each separately and independently movable. Moreover, note that these speaker assemblies are not positioned about the satellite 20 at a uniform distance from the central vertical axis 76 (FIGS. 1 and 3). That is, although most of the speaker assemblies 24a and 24b are substantially tangential to the locus of points indicated by the circle 80 (centered at the central vertical axis 76), some of the speaker assemblies are displaced nearer or further away than the radial distance of the circle 80. Moreover, some of the speaker assemblies 24a and 24b have their acoustic output angled somewhat away from the central vertical axis 76. Such deviations in distance and direction of the speaker assemblies 24a and 24b are the result of calibrating speaker assembly acoustical output at various points about the satellite 20. That is, it is an aspect of the present invention to calibrate the acoustic output of the speaker assemblies 24a and 24b so that:

(a) there is substantially uniform acoustic pressure being directed to at least a majority (and preferably in some embodiments substantially all) of the outermost sides of the satellite 20 at the same time. For example, such uniform acoustic pressure may vary by, in general, no more than 6 dB from the acoustic test specification tolerance on individual third octave bands;

(b) the desired acoustic range and decibel level are attained at least most of the outermost satellite 20 surfaces; and (c) there are no extreme acoustic anomalies (e.g., high intensity resonance locations or acoustically dampened locations) at or near the satellite 20, wherein such anomalies have acoustic intensity deviations sufficiently far from the desired acoustic test specifications so as to damage the satellite 20 and/or compromise the validity of the acoustic testing being performed.

Accordingly, to satisfy (a)–(c) immediately above, the position and acoustic direction of the output of each speaker assembly 24a and 24b may be adjusted during a calibration process of the present invention. To obtain acoustic data for accomplishing such physical adjusting of the speaker assemblies as well as electronic balancing the acoustic output between the speaker assemblies, microphones 84 are placed near and about the test object (e.g., satellite 20) for measuring the acoustic output of the speaker assemblies. In the embodiment of FIGS. 1–3, each microphone 84 is approximately 6 inches from an outermost surface of the satellite 20. Based on this, it is noted that at least one, and preferably at least a majority, of the microphones 84 are located at a radial distance from the central vertical axis 76 that is less than the radial distance from the central vertical axis 76 to at least a majority of the speaker assemblies 24, if not all of the speaker assemblies 24. Moreover, one or more of the microphones 84 may be located at a location whereby they can measure an expected maximal acoustic pressure of one or more of the speakers 36, 40 and 44. In particular, the microphone 84 shown in FIG. 3 is located so as to measure an expected locally maximal acoustic pressure output by the two tweeters 40 of adjacent speaker assemblies 24a and 24b. Other microphones 84 placed about the satellite 20 (FIG. 1) provide similar acoustic measurements for the tweeters 40 and/or for one or more of the other speaker types 36 and 44. Moreover, the microphones 84 may also be positioned about the satellite 20 so as to measure the acoustic speaker output at locations that are expected to have a relatively reduced or dampened acoustic intensity at one or more frequency ranges.

Additionally, embodiments of the present invention may also utilize outputs from one or more movable microphones 84 that can be moved about the test object during activation of the speaker assemblies 24a and 24b, wherein such movable microphones are for identifying local acoustic minima and maxima. In particular, for the embodiment of FIGS. 1–3, the satellite 20 is shown in FIG. 3 as having an upper portion 88 extending through the ceiling of the enclosure 96 (this enclosure containing most of the satellite and all of the speaker assemblies 24a and 24b). Accordingly, during calibration of the acoustic output for the present invention, at least one roving microphone 84 may be provided for moving about the space near the upper portion 88 for determining the acoustic characteristics there. In performing acoustic measurements in the space near the upper portion 88 of the satellite, it is worthwhile to note that in at least one such calibration test, the roving microphone 84 identified locations therein of high acoustic intensity believed to be local resonances produced primarily from acoustic reflections from the surfaces of the satellite 20. Moreover, note that to mitigate or dampen such locations of local acoustic build-up, the enclosure 96 may be provided with acoustic dampening material on the interior walls of the enclosure 96. Accordingly, in at least one embodiment, the enclosure 96 may have sufficient sound dampening characteristics so as to be substantially anechoic.

Figure 4:
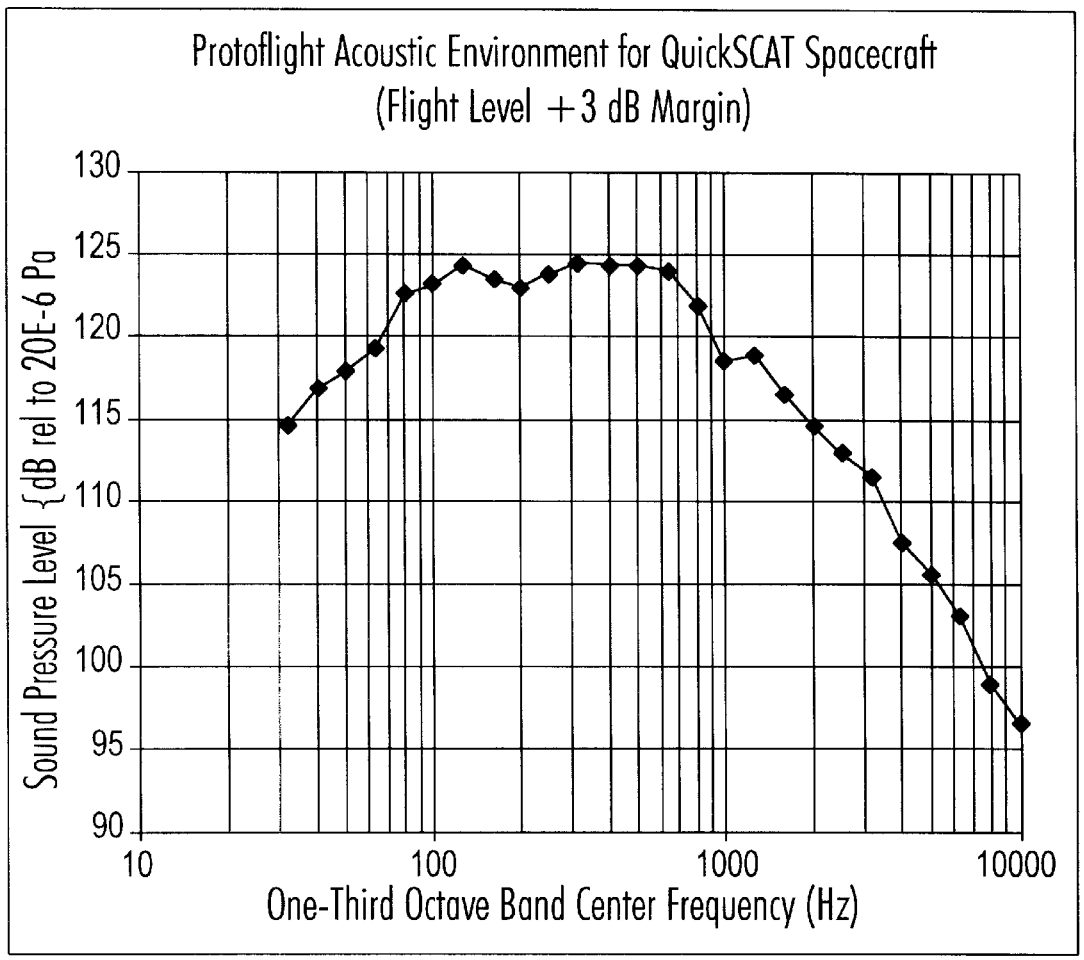

Table 2 hereinbelow, lists the frequencies and their corresponding desired decibel levels (relative to 20 microPascal) to be obtained when testing the satellite 20. Note that the frequencies are every third octave band within the test range of 30 Hz to 10,000 Hz, and FIG. 4 provides a corresponding graph obtained from connecting the sample points of Table 2. Accordingly, the present invention provides a technique for using the acoustic measurements obtained from the microphones 84 for determining when the speaker assemblies 24a and 24b surrounding the satellite 20 are within a predetermined tolerance of the acoustic test specification sample test points as represented in Table 2 and FIG. 4.

TABLE 2

Protoflight Acoustic Level

| One-Third Octave Band Center Frequency (Hz) | Sound Pressure Level (dB) |
|---|---|
| 31.5 | 114.6 |
| 40 | 116.8 |
| 50 | 117.8 |
| 63 | 119.2 |
| 80 | 122.7 |
| 100 | 123.2 |
| 125 | 124.3 |
| 160 | 123.4 |
| 200 | 123 |
| 250 | 123.8 |
| 315 | 124.5 |
| 400 | 124.3 |
| 500 | 124.3 |
| 630 | 124 |
| 800 | 121.8 |
| 1000 | 118.5 |
| 1250 | 118.8 |
| 1600 | 116.5 |
| 2000 | 114.5 |
| 2500 | 113 |
| 3150 | 111.5 |
| 4000 | 107.6 |
| 5000 | 105.7 |
| 6300 | 103.1 |
| 8000 | 99 |
| 10000 | 96.5 |
| OASPL | 134.8 |

Moreover, regarding the graph of FIG. 4, it is worthwhile to note that the shape and decibel levels of the graph provided therein are similar to many other acoustic testing specifications for satellites.

To determine whether the speaker assemblies 24a and 24b surrounding the satellite 20 provide an acoustic output within a predetermined tolerance of a desired specification (e.g., Table 1 and FIG. 4), the speaker assembly outputs are also balanced during the calibration process at each of the sample test points. Thus, for each pair of frequency (f), and corresponding decibel level (d) constituting one of the sample test points, the expected result of the balancing is that the acoustic output from the speaker assemblies 24a and 24b is a substantially uniform acoustic pressure of d at substantially all outermost surfaces of the satellite. Moreover, such uniformity may be quantified as substantially within a range of 6 dB of d. So that each microphone 84 measures a decibel level within this range at each frequency f.

Figure 5B:
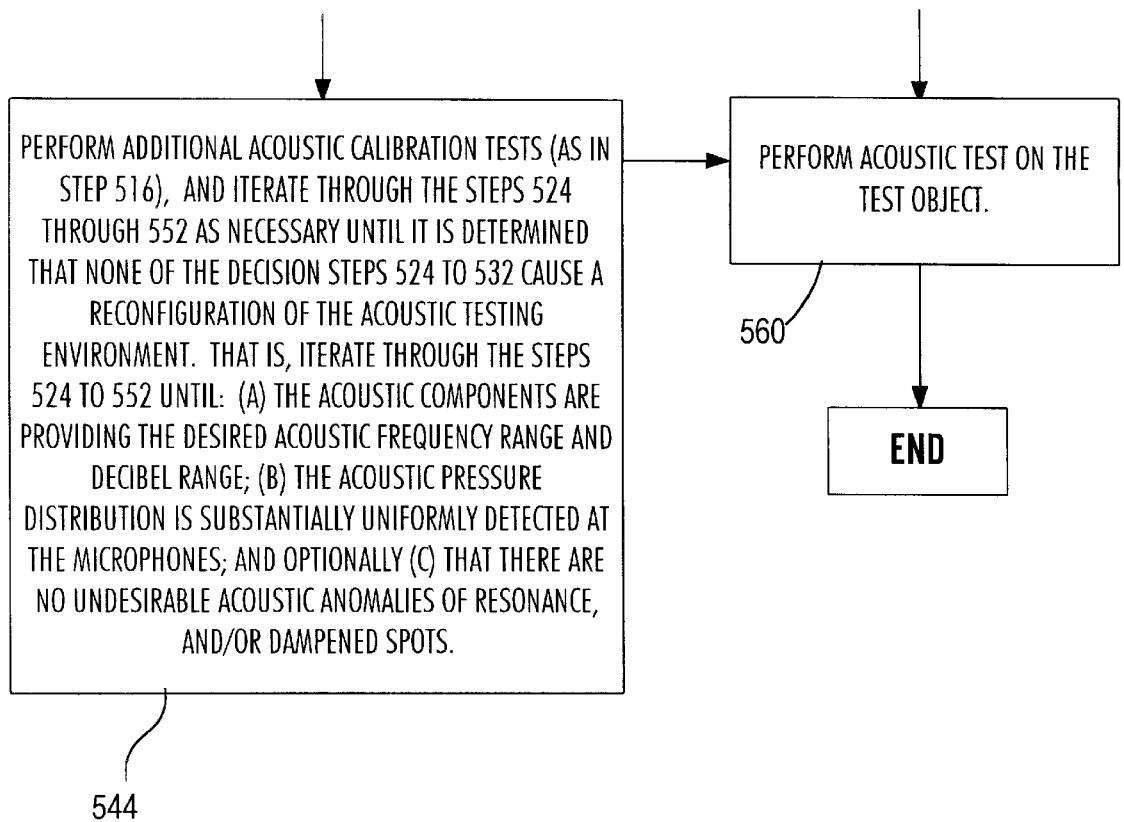

FIGS. 5A and 5B show the high level steps performed during the process of calibrating the acoustic components for the present invention (e.g., speaker assemblies 24a and 24b, plus amplifiers and other acoustical devices referred to hereinabove). In particular, the process of calibrating is performed prior to acoustically testing a test object such as satellite 20. Accordingly, in step 504, the acoustic components of the present invention are determined for generating the acoustic frequency range and decibel range desired for testing. FIGS. 1–3 and the corresponding description provide one such embodiment of the acoustic components of the present invention. Further, note that the determination of acoustic components in step 504 also includes determining appropriate amplifiers, pink noise generators as one skilled in the art will understand.

In one particular embodiment of step 504 having substantial similarity to the embodiment illustrated in FIGS. 1–3 together with acoustical specification of FIG. 4, fifteen speaker assemblies 24 plus one additional non-stacked speaker cabinet was determined to be sufficient to obtain an overall acoustic pressure of 135 dB at one meter in front of the speakers when the speakers were driven with 40,000 rms watts, wherein overall acoustic pressure is calculated as follows:

Step 1: Determine the sound pressure measurement $MSP_1$ for each third octave band, i, of Table 2 as follows:

$$MSP_i = (P_{REF})10^{\left(\frac{dB_i}{10}\right)}$$

where
PREF is $2.0 \times 10^{-5}$ Pascals, and
dBi is the sound pressure level of the $i^{th}$ third octave band, wherein the average is taken over the measurements obtained from the eight microphones 84.

Step 2: Determine the total sound pressure TSP:

$$TSP = \sum_i MSP_i,$$

i varies over each third octave band of Table 2.

Step 3: Determine the overall sound pressure level, OASPL:

$$OASPL = 10 \log\left[\frac{TSP}{(P_{REF})^2}\right]$$

In step 508 of FIG. 5A, the speakers of the acoustic components are placed in approximate positions around the test object such that there is likely to be an approximately uniform acoustic pressure for each desired testing frequency, directed at and also surrounding the test object. Note that, in general, the positioning of the speakers may be substantially determined by determining approximate distances from the test object, wherein the distances are determined, at least in part, by: (a) the maximum desired decibel testing levels, (b) the acoustic components selected, and (c) theoretically and/or empirically determined acoustical characteristics of the interaction between the speaker outputs, the test object, and the enclosure in which the speakers and test object are contained. For instance, it is known that there is typically approximately a 6 dB decrease with each doubling of distance from an acoustic point source.

Subsequently, in step 512, microphones (e.g., microphones 84) are placed in approximate positions around the test object, wherein the microphones are between the test object and the speakers. Note that the microphones may be placed relatively near the test object (e.g., approximately 6 inches therefrom in the embodiment of FIG. 1 and preferably no greater than about 12 inches) for measuring the decibel level substantially at the test object. Moreover, one or more microphones may be placed so as to measure at least one of a maximal and minimal acoustic pressure impacting the test object. Note that the positioning of the microphones at expected maximal and minimal acoustic locations can be initially approximated by sampling the acoustic environment at various locations when the speakers are activated.

In step 516, an initial acoustic test for calibrating the acoustic pressure directed at the test object is performed for determining: (a) whether the acoustic components are providing the desired acoustic frequency range and decibel range, (b) whether the acoustic pressure distribution is substantially uniformly detected at the microphones, and optionally (c) whether there are undesirable acoustic anomalies of resonance and/or acoustically dampened locations within the acoustic environment. Note that during this test, acoustic measurements are collected from the microphones. For instance, referring to the embodiment of FIGS. 1–4, this initial acoustic test may include activating the speaker assemblies 24a and 24b at each of the third octave bands of Table 2, and determining whether the corresponding decibel ranges of Table 2 are substantially uniformly achieved at the microphones 84. Subsequently, in step 524, a determination is made, from the acoustic measurements collected, as to whether the current configuration of acoustic components provides the desired test specification frequencies in corresponding decibel ranges. If step 524 is answered in the affirmative, then step 528 is performed wherein a determination is made as to whether the acoustic distribution is adequately uniform about the test object. If so, then, optionally, the step 532 is performed for determining whether there is one or more undesirable acoustic anomalies such as an out of specification acoustic measurement at or near the test object, wherein this measurement is either above or below a desired decibel level tolerance. Subsequently, if there are no such undesirable anomalies, then step 560 is performed wherein the test object is subjected to a full scale acoustic testing over the desired test range of frequencies and corresponding decibel levels, such as those in Table 2 and FIG. 4. Note that in the embodiments of FIGS. 1–3, such acoustic testing may be done in conjunction with mechanical vibration testing. Further note that during such testing and/or immediately thereafter, the test object may be activated for determining if there are any electronic or mechanical malfunctions induced by the test.

Returning now to step 524, if it is determined that the acoustic components do not provide the desired frequency range and/or decibel range, then in step 540 one or more of the acoustic components are replaced and/or additional acoustic components are provided. In particular, in the embodiment of FIGS. 1–3, additional speaker cabinets 28 and 32 may be stacked upon one another and/or suspended above or adjacent to the satellite 20 for providing a more uniform acoustic pressure distribution and/or test at higher decibel levels.

Alternatively, if in step 528 it is determined that the acoustic pressure is inadequately uniformly distributed, then step 544 is performed wherein the speaker output levels are balanced, and/or the speaker positions are adjusted. Note that such speaker position adjustments may, in general, be performed by directing speaker outputs more toward or away from one or more of the microphones by an angular adjustment and/or an adjustment in distance (radial and/or vertical) relative to the microphones. Additionally, note that the microphone positions may also be adjusted in some cases to correspond with the new speaker positions. In particular, such adjustment in microphone positions may be performed when there is substantial rearrangement of the speakers.

If in step 532 it is determined that there are undesirable acoustic anomalies, then step 548 is performed wherein for undesirable resonances of high acoustic intensity (relative to the testing specification), the speaker positions may be adjusted and/or dampening material may be added, e.g., to the walls of the enclosure housing the speakers and the test object. Additionally, partitions (not shown) between speakers (or speaker components) may be utilized for physically disbursing and/or inhibiting such acoustic intensity buildups. Alternatively, if there are locations where the acoustics are undesirably dampened, then the location of the speakers may be adjusted and/or additional speakers may be added. It is worthwhile to note the distinctions between what is being determined in the steps 524, 528 and 532. For instance, step 524 determines whether sufficient acoustic energy can be provided for testing the test object at the desired decibel levels and frequencies, whereas step 528 determines whether there is a substantially uniform acoustic pressure throughout the space adjacent to the test object, and step 532 determines whether there are isolated relatively confined acoustic anomalies near the test object that may require minor adjustments in the positioning of the speakers and/or other techniques (e.g., partitions) for remedying the anomalies.

Subsequent to any one of the steps 540, 544 and 548, step 552 is performed wherein the steps 524–552 are repeated as necessary until it is determined that decision steps 524–532 yield a satisfactory acoustic environment to perform the actual acoustic test on the test object. Accordingly, once a satisfactory acoustic environment is obtained, then step 560 is encountered for performing the acoustic test on the test object.

Figure 6:
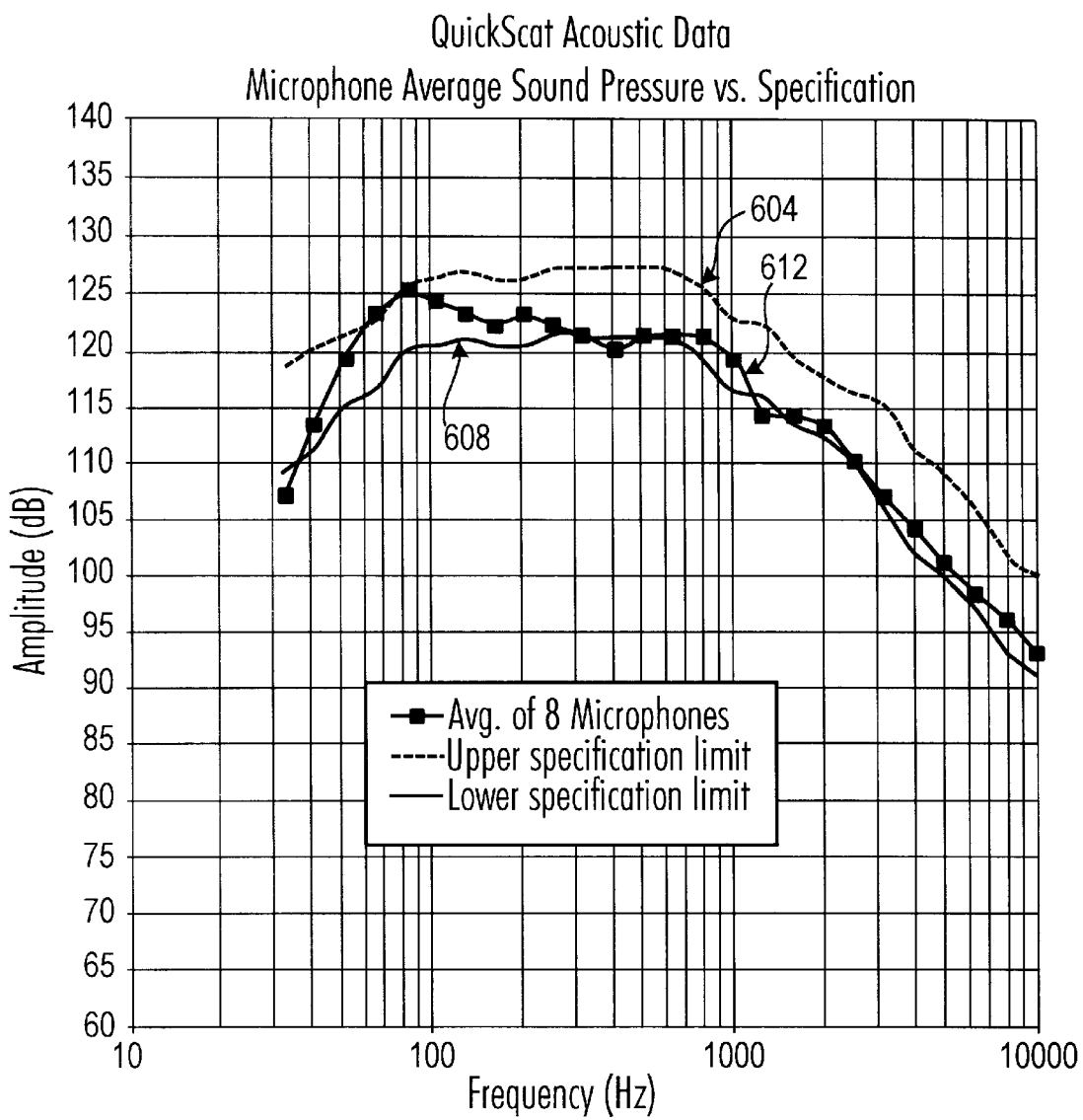
Figure 7:
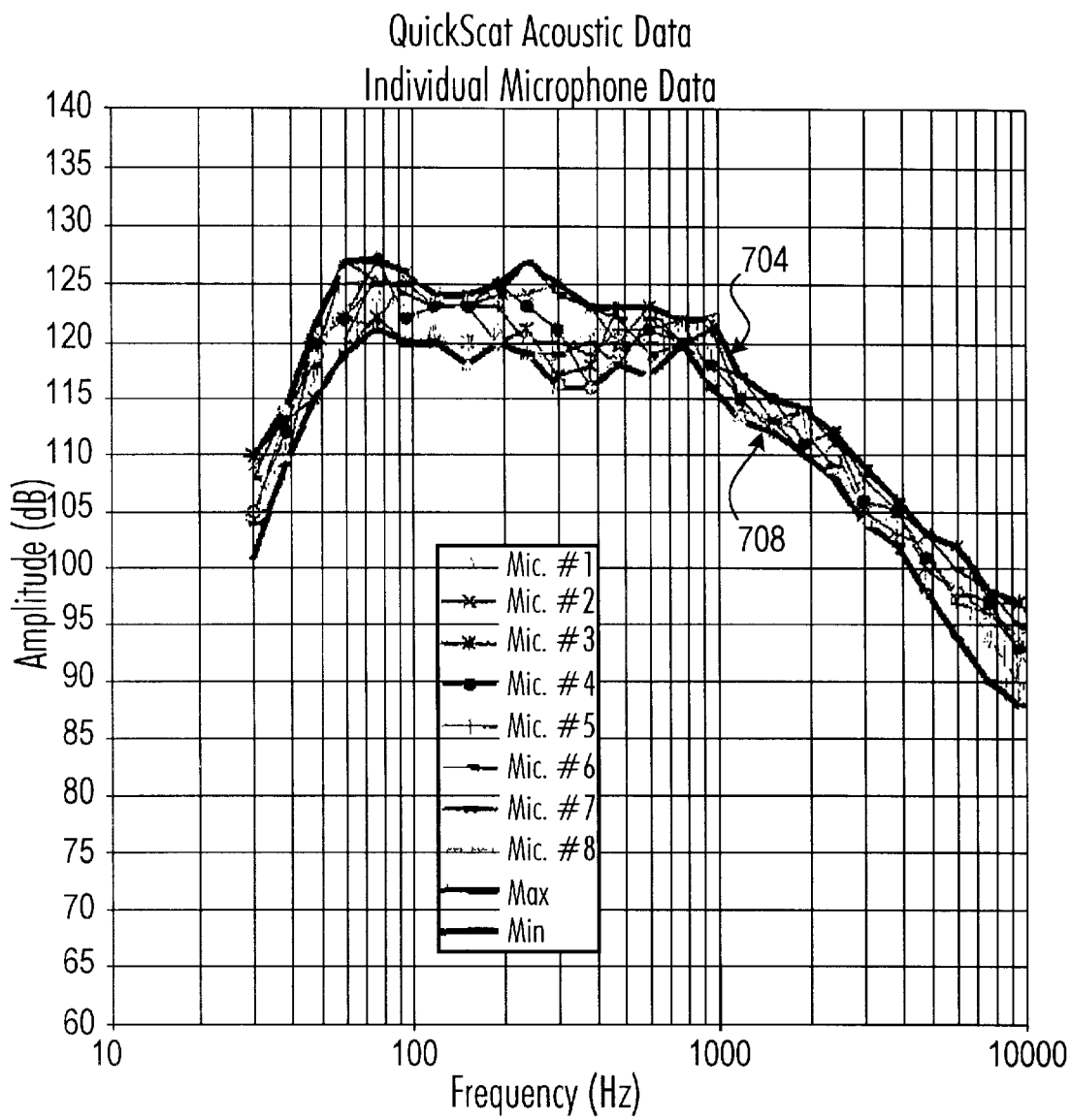

FIGS. 6 and 7 show outputs of the embodiment of the present invention of FIGS. 1–3 as it applies to the testing of satellite 20. In particular, the testing specification sample test points used are those identified in Table 2 and FIG. 4. Regarding FIG. 6, the graphs 604 and 608, respectively, represent the high and low test specification tolerances for substantially maximal deviations from the specification sample test points. Additionally, the graph 612 shows the average frequency/amplitude response for all eight of the microphones 84. Accordingly, it can be seen that the acoustic output for the test is substantially within the desired range between the graphs of the high and low tolerances.

Regarding FIG. 7, this figure shows the graphs of each of the individual microphones 84 whose values were used to determine the average graph of FIG. 6. Note that although the maximal tolerances are not shown on this figure, the minimum and maximum graphs 704 and 708 are substantially within the high and low test specification tolerances of the graphs 604 and 608. It is also worth noting that much of the deviation between, e.g., the average graph and the specification points was due to an error in determining the desired output from the speaker assemblies 24a and 24b.

There are numerous alternative embodiments for the present invention that may be utilized. For example, in the embodiment of FIG. 1, the output of the speaker assemblies 24a and 24b may be phased so that, e.g., the speaker assemblies are partitioned into groups, wherein each group extends angularly approximately 90° about the satellite 20, and wherein each of the four resulting groups are out of phase with each other. Accordingly, this may alleviate certain acoustic resonance build-ups as well as reducing certain acoustic feedbacks to the microphones 84 as one skilled in the art will understand. Additionally, in at least some embodiments of the present invention, the speakers providing direct acoustic impact on the test object need not completely surround the test object. In particular, such partially surrounding acoustic testing may be advantageous when testing certain components of a spacecraft such as solar arrays, antennas and other spacecraft panels with significant panel surface area and low density which would be susceptible to acoustic excitation, e.g., a spacecraft shear panel with little or no components installed. Moreover, such partially surrounding direct acoustic output may be used for validating design changes made to a portion of a spacecraft, wherein the rest of the spacecraft has been previously determined to be acoustically acceptable and/or it is known that the portion being tested is potentially acoustically more vulnerable than other portions of the spacecraft. Moreover, such partially surrounding acoustic testing may be useful for acoustic requalification of spacecraft components having upgraded hardware. Note that in performing such a partially surrounding test, in general, at least an angle of approximately 90° about the test object is preferred. Thus, the present invention provides direct acoustic impact on the test object from substantially more than a single point acoustic source. Additionally, at least one-quarter of the outermost surface area of the test object may be simultaneously acoustically impacted. Moreover, it is also within the scope of the present invention that the speakers (more generally acoustic output devices) may substantially surround the test object in a spherical or a semispherical configuration.

The foregoing discussion of the invention has been presented for purposes of illustration and description. Further, the description is not intended to limit the invention to the form disclosed herein. Consequently variation and modification commiserate with the above teachings, and within the skill and knowledge of the relevant art, are within the scope of the present invention. The embodiments described hereinabove are further intended to encompass the best mode presently known of practicing the invention, and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A system for testing an object including acoustic testing thereof, comprising:
    a plurality of audio output assemblies including at least a first audio output assembly and a second audio output assembly, said plurality of audio output assemblies being spaced from and located about the object, said plurality of audio output assemblies being controlled by at least a first electrical driving signal and outputting acoustic wave signals; and
    at least a first microphone located between said plurality of audio output assemblies and the object, said first microphone for receiving at least portions of said acoustic wave signals;
    wherein said acoustic wave signals are output from said plurality of audio output assemblies in an angle of at least 90° about the object.

2. The system, as claimed in claim 1, wherein:
    at least said first and second audio output assemblies are moveable relative to the object from a first orientation to a second orientation, wherein said acoustic wave signals are provided to the object at both said first orientation and said second orientation.

3. The system of claim 1, wherein said second orientation is different from said first orientation by at least one of:
    a distance from the object, a direction for generating a portion of said acoustic wave signals, and a height.

4. The system, as claimed in claim 1, wherein:
    said first audio output assembly is located closer to the object than said second audio output assembly.

5. The system, as claimed in claim 1, wherein:
    said first microphone is located closer to the object than to each of said plurality of audio output assemblies.

6. The system, as claimed in claim 1, wherein:
    said plurality of audio output assemblies are located at a determined distance from the test object, said determined distance being determined using at least a plurality of the following: (a) a maximum desired decibel testing level, (b) capabilities of acoustic components of said plurality of audio output assemblies, and (c) information related to an interaction among said audio output assemblies, the object and an enclosure in which said audio output assemblies and object are situated.

7. The system, as claimed in claim 1, wherein:
    said first microphone provides information related to at least a plurality of the following: (a) whether said acoustic wave signals provide desired decibel levels and frequencies for testing the object, (b) whether substantially uniform acoustic pressure is present adjacent to the object, and (c) whether acoustic anomalies exist adjacent to the object.

8. The system, as claimed in claim 1, wherein:
    said acoustic wave signals have an acoustic pressure associated therewith and in which said acoustic pressure is ascertained by: (a) determining a sound pressure measurement, (b) determining a total sound pressure and (c) determining an overall sound pressure level.

9. A method for testing an object including acoustic testing thereof, comprising:
    providing a plurality of audio output assemblies including at least a first audio output assembly and a second audio output assembly and in which said plurality of audio output assemblies are spaced from and located about the object;
    first outputting acoustic wave signals by said plurality of audio output assemblies towards the object, wherein said acoustic wave signals are expected to approximate a plurality of desired frequencies and corresponding acoustic pressure levels;
    obtaining information related to said acoustic wave signals;

determining whether said acoustic wave signals are to be changed based on said information;

adjusting said acoustic wave signals when said step of determining determines that said acoustic wave signals are to be changed for better approximating said plurality of desired frequencies and corresponding acoustic pressure levels; and second outputting said adjusted acoustic wave signals by said plurality of audio output assemblies, wherein said adjusted acoustic wave signals acoustically test whether an operable feature of the object remains operable.

10. A method, as claimed in claim 9, wherein:

said providing step includes providing at least a first microphone and locating said first microphone between said plurality of audio output assemblies and the object and said obtaining step includes receiving at least portions of said acoustic wave signals by said first microphone.

11. A method, as claimed in claim 9, wherein:

said providing step includes positioning said plurality of audio output assemblies around at least a majority of a perimeter of the object.

12. A method, as claimed in claim 9, wherein:

said outputting step includes outputting said acoustic wave signals from an angle of at least 90° about the object.

13. A method, as claimed in claim 9, wherein:

the object has a total outermost surface area and said outputting step includes outputting said acoustic wave signals at the same time to at least one-quarter of the total outermost surface area of the object.

14. A method, as claimed in claim 9, wherein:

said determining step includes determining distances between said plurality of audio output assemblies and the object and in which the distances are determined using information related to a plurality of (a)–(c) following: (a) a maximum desired decibel testing level, (b) acoustic components associated with said plurality of audio output assemblies, and (c) acoustical characteristics of interaction between said acoustic wave signals output by said audio output assemblies, the object and an enclosure in which said audio output assemblies and the object are contained.

15. A method, as claimed in claim 9, wherein:

said determining step includes first establishing whether said acoustic wave signals provide said desired acoustic frequency range and decibel range, and second establishing whether acoustic pressure distribution is substantially uniform at least a portion of the object.

16. A method, as claimed in claim 15, wherein:

said determining step includes determining the presence of acoustic anomalies of resonance and acoustically dampened locations relative to the object.

17. A method, as claimed in claim 9, wherein:

said determining step includes determining an acoustic pressure that is ascertained using: (a) a sound pressure measurement, (b) a total sound pressure, and (c) an overall sound pressure level.

18. A method, as claimed in claim 9, wherein:

said adjusting step includes moving at least said first audio output assembly relative to the object.

19. A method, as claimed in claim 18, wherein:

said moving said first audio output assembly includes at least one of: (a) radially moving said first audio output assembly relative to the object, (b) vertically moving said first audio output assembly relative to the object, and (c) modifying an angle of said first audio output assembly relative to the object.

20. A method, as claimed in claim 9, further including:

vibrating the object in the same enclosure in which said step of second outputting is performed.

21. A method, as claimed in claim 9, wherein at least said obtaining, determining and adjusting steps are part of acoustic calibrating procedure.

* * * * *